United States Patent [19]

Conrad et al.

[11] Patent Number: 5,280,016

[45] Date of Patent: Jan. 18, 1994

[54] NON-ANTICOAGULANT HEPARIN DERIVATIVES

[75] Inventors: H. Edward Conrad; Yuchuan Guo, both of Alameda, Calif.

[73] Assignee: Glycomed Incorporated, Alameda, Calif.

[21] Appl. No.: 753,299

[22] Filed: Sep. 3, 1991

Related U.S. Application Data

[63] Continuation-in-part of Ser. No. 677,406, Mar. 29, 1991, abandoned.

[51] Int. Cl.$^5$ .................... A61K 31/725; C08B 37/10
[52] U.S. Cl. ...................... 514/56; 514/54; 536/21; 536/55.3; 536/55.1; 536/53; 536/54; 536/55
[58] Field of Search ............... 536/21, 55.3, 54, 55.1, 536/53, 55; 514/56, 54

[56] References Cited

U.S. PATENT DOCUMENTS

| | | | |
|---|---|---|---|
| 3,135,660 | 6/1964 | Bush et al. | 536/21 |
| 4,791,195 | 12/1988 | Bianchini et al. | 536/21 |
| 4,933,326 | 6/1990 | Bianchini et al. | 514/56 |
| 4,990,502 | 2/1991 | Lormead et al. | 514/56 |
| 5,032,679 | 7/1991 | Brandley et al. | 536/21 |

FOREIGN PATENT DOCUMENTS 0268885 6/1988 European Pat. Off. .
3519011 11/1986 Fed. Rep. of Germany .

OTHER PUBLICATIONS

Fransson et al; Febs Letters 97(1):119–123 (1979).
Fransson et al; Carbohydrate Research 80:131–145 (1980).
Castellot, Jr. et al; Journal of Cellular Physiology 120:315–320 (1984).
Casu et al; Arzneim.-Forsch./Drug Research 36(I), Nr. 4:637–642 (1986).
Fransson; Carbohydrate Research 62:235–244 (1978).
Austin et al., J. Am. Coll. Cardiol. (1985) 6:369–375.
Bienkowski et al., J. Biol. Chem. (1985) 260:356–365.
Guo et al., Analyt. Biochem. (1988) 168:54–62.
Guo et al., Analyt. Biochem. (1989) 176:96–104.
Clowes et al., Nature (1977) 265:625–626.
Marcum et al., Biology of Proteoglycan Academic Press, (1987), pp. 301–343.
Castellot, Jr., et al., J. Biol. Chem. (1982) 257:11256–11260.
Benitz et al., J. Cell. Physiol. (1986) 127:1–7.
Orlidge et al., Microvascular Research (1986) 31:41–53.
Castellot, Jr. et al., J. Cell. Biol. (1986) 102:1979–1984.
Barzu et al., J. Cell. Physiol. (1989) 140:538–548.
Wright et al., J. Biol. Chem. (1989) 264:1534–1542.

Primary Examiner—Nancy S. Carson
Attorney, Agent, or Firm—Kate H. Murashige; Gregory J. Giotta

[57] ABSTRACT

A non-anticoagulant (NAC) form of heparin which shows antiproliferative activity with respect to smooth muscle cells is useful in the prevention of restenosis and other conditions benefited by antiproliferative activity with respect to smooth muscle cells. This NAC form of heparin is prepared by oxidizing heparin/heparan sulfate to a desired level with periodate followed by reduction of the resulting aldehyde groups; all under conditions which prevent depolymerization of the heparin.

12 Claims, 2 Drawing Sheets

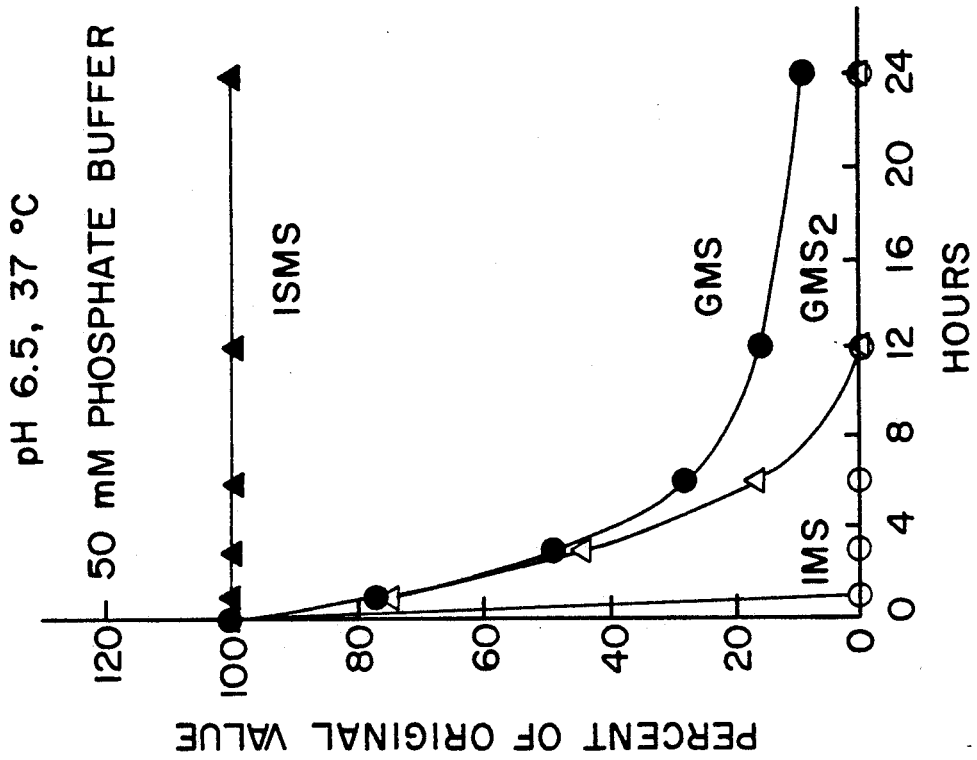
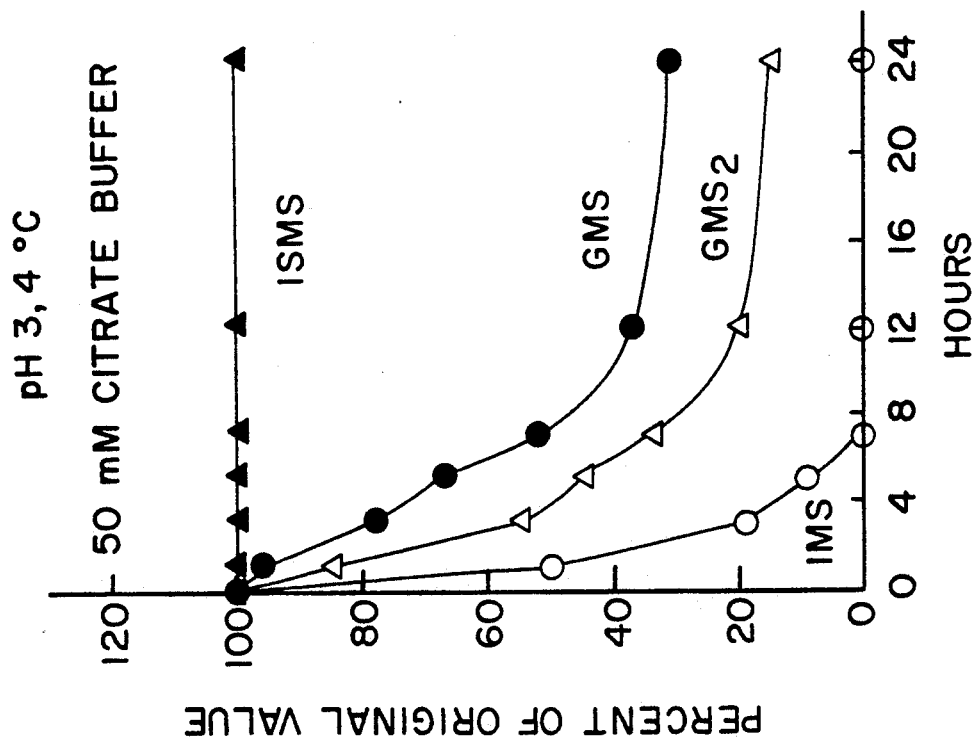

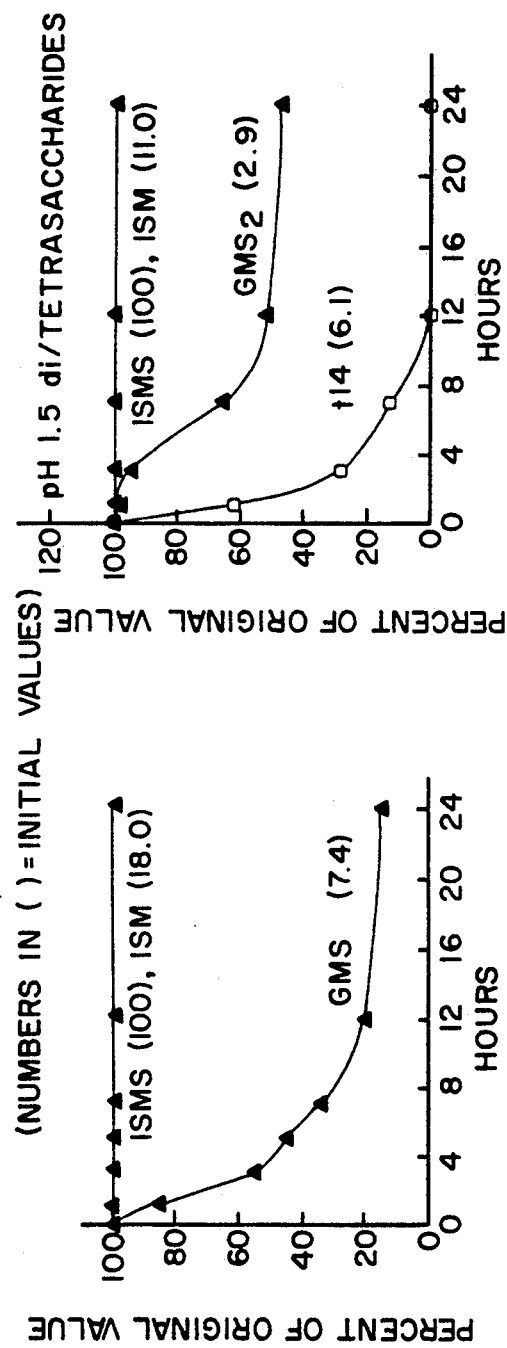
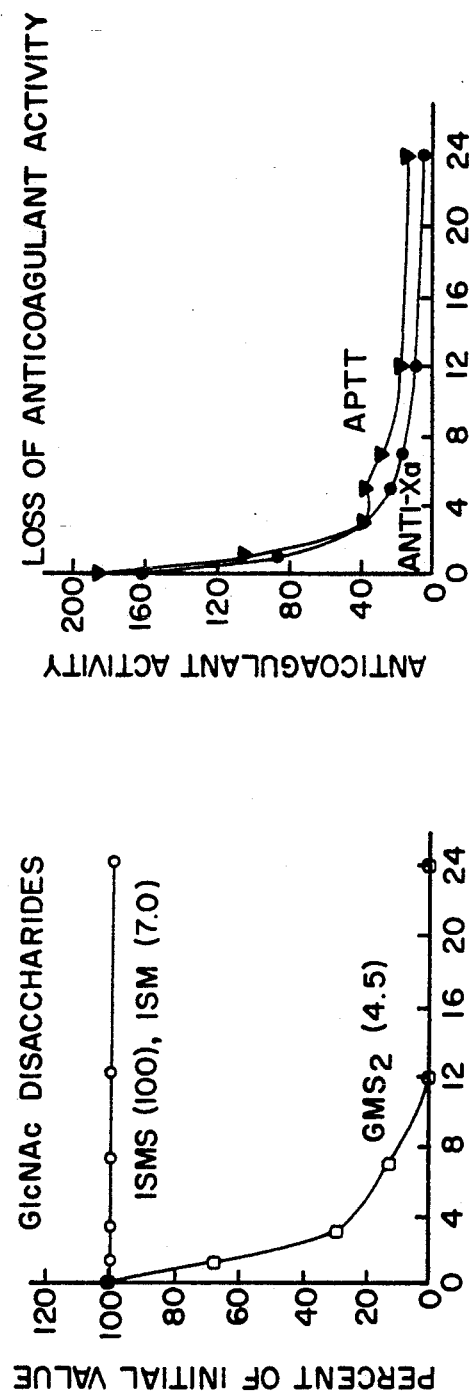

NON-ANTICOAGULANT HEPARIN DERIVATIVES

CROSS-REFERENCE TO RELATED APPLICATION

This application is a continuation-in-part of U.S. Ser. No. 07/677,406, filed Mar. 29, 1991, now abandoned.

TECHNICAL FIELD

The invention relates to heparin-derived pharmaceutical compositions which are useful as antiproliferative and antithrombotic agents but lack anticoagulant activity. More particularly, the invention concerns substantially full-length heparin oligomers which have been depleted of anticoagulant activity but not antiproliferative activity by oxidation with periodate and reduction of the resulting aldehydes under conditions which prevent fragmentation of the heparin.

ABBREVIATIONS

The following abbreviations are used for monosaccharides or for monosaccharide residues included in oligomers: D-glucuronic acid=GlcA; L-iduronic acid=IdoA; D-glucosamine=GlcNH$_2$; N-acetyl-D-glucosamine= GlcNAc; D-glucosamine N-sulfate=GlcNS; 2,5-anhydromannose=AMan; 2,5-anhydromannitol=AManH.

In designating each saccharide residue, below the appropriate abbreviation, the location of the O-linked sulfate residues is indicated by "S" and the number of the position of sulfation where the sulfate residue is linked to oxygen on the sugar residue. In the designations for heparin structure, also, the positions involved in the alpha and beta anomeric linkages are as those conventionally found in heparin, α (glucosamine → uronic) and β (uronic glucosamine), and the D or L configurations as conventionally found pertains. The locations of the sulfates are shown below the abbreviation for the sugar to which they apply, thus, for example, IdoA—GlcNS
2S    6S refers to a dimer of L-iduronic acid and D-glucosamine N-sulfate-linked β(1-4) with sulfates connected respectively at the 2 and 6 positions of the sugar residues.

BACKGROUND ART

Proliferation of smooth muscle cells in blood vessel walls occurs in response to vascular injury, and in association with certain disease states (Austin, G.E., et al., *J Am Coll Cardiol* (1985) 6:369–375). The proliferation of these cells can have negative effects due to the production of excess proteins or other matrix molecules, which, along with the cells themselves, form pathologic lesions of, for example, atherosclerosis, renal hypertension, pulmonary hypertension, vasculitis, and post-surgical vascular restenosis. These results are distinguished from the acute response to trauma characterized by blood clotting.

Heparin/heparan sulfate is known to inhibit smooth muscle cell proliferation. Heparin/heparan sulfate is a member of a class known as glycosaminoglycans (GAG). These materials are copolymers of alternating hexosamine and aldouronic acid residues which are found in sulfated forms and are synthesized as proteoglycans.

In the compositions of interest herein, heparan sulfate and heparin, the hexosamine is mostly N-acetylated or N-sulfated glucosamine (GlcNAc and GlcNS), and the aldouronic acid is mostly L-iduronic in heparin and mostly D-glucuronic acid in heparan sulfate. Heparan sulfate is commonly considered to have a higher proportion of glucuronic acid than heparin.

Problems of heterogeneity in preparations of heparan sulfate or heparin isolated from tissues make sharp distinctions difficult, since these oligosaccharides are related by their biosynthesis pathway, as explained below. Conventional heparin (used as an anticoagulant) has a molecular weight of 5–25 kd and is extracted as a mixture of various chain lengths by conventional procedures. These procedures involve autolysis and extraction of suitable tissues, such as beef or porcine lung, intestine, or liver, and removal of nonpolysaccharide components.

The molecular weight of the chains in the extract is significantly lower than the 60–100 kd known to exist in the polysaccharide chains of the heparin proteoglycan synthesized in the tissue. The GAG moiety is synthesized bound to a peptide matrix at a serine residue through a tetrasaccharide linkage region of the sequence D-GlcA-D-Gal-D-Gal-D-Xyl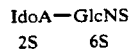protein, which is then elongated at the D-GlcA residue with alternate additions of GlcNAc and GlcA.

The polysaccharide side chains are modified by a series of enzymes which sequentially deacetylate the N-acetyl glucosamine and replace the acetyl group with sulfate, epimerize the hydroxyl at C5 of the D-glucuronic acid residue (to convert it to L-iduronic acid and the GAG chain from the heparan type to a heparin type), sulfate the O-2 of the resulting L-iduronic acid and the O-6 of the glucosamine residue. Some of the chains are further sulfated at the O-3 of the glucosamine residue, either at the heparan or heparin stage. This further sulfation is associated with the active site for binding to antithrombin III (ATIII) which is associated with anticoagulant activity. A synthetic pentasaccharide sequence capable of binding ATIII has been identified as

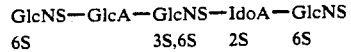

by Choay (French Application No. 2,535,324). However it appears that the sequence in heparin corresponding to this pentasaccharide is generally

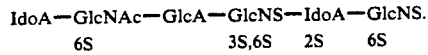

Other chemically possible sulfation sites are on the O-3 of L-iduronic or D-glucuronic and O-2 of D-glucuronic acid; however, these are seldom found.

Due to their obvious chemical similarity, isolated "heparin" may contain considerable amounts of what might otherwise be classified as heparan sulfate.

There is an extensive body of art concerning depolymerization of heparin/heparan sulfate chains and separation of products by size. In a generally used procedure, the heparin starting material is depolymerized in the presence of nitrous acid with or without pretreatment to remove acylation from any GlcNAc residues present. Nitrous acid, under the appropriate conditions, cleaves at the linkage between a GlcNS or GlcNH$_2$ residue and the uronic acid residue through which it is linked through a glucosamine α(1-4) uronic acid linkage. If the heparin has been deacetylated, all of the glucosamine→ uronic acid residues are susceptible and complete depolymerization results in disaccharides. If the heparin has not been deacetylated, the glucosamine→ uronic acid residues wherein the glucosamine is acetylated are resistant, and both disaccharides and tetrasaccharides containing the resistant linkage result. In all cases, the glucosamine residue at the reducing terminus of the disaccharide or tetrasaccharide is converted to a 2,5-anhydromannose in the course of cleavage. This residue may further be reduced to the corresponding 2,5-anhydromannitol. These methods have been described by Bienkowski, M.J. and Conrad, H.E., *J Biol Chem* (1985) 260:356-365; Guo, Y., et al., *Anal Biochem* (1988) 168:54-62; and Guo, Y. and Conrad, H.E., *Analyt Biochem* (1989) 176:96-104. These methods are useful in analyzing the structure of heparin and in assessing the results of various treatments of the heparin chains. Further, there has been considerable attempt to use the products of degradation of heparin from both complete and partial digestion with nitrous acid as described in the foregoing papers, or from heparinase digestion or from periodate oxidation followed by β-elimination. All of these processes generate low molecular weight heparins for therapeutic use.

The involvement of heparin or heparan sulfate or degradation products thereof in smooth muscle proliferation has been recognized for some time. Heparin and heparan sulfate can slow or arrest the vascular proliferation associated with injury described hereinabove (Clowes, A.W., et al., *Nature* (1977) 265:625-626). The effect of heparan sulfate and heparin on smooth muscle proliferation is also described by Marcum, J.A., et al. in *Biology of Proteoglycan*, Academic Press (1987) pp. 301-343 The inhibition of vascular smooth muscle cell growth by heparin was further described by Castellot, J.J., Jr., et al., *J Biol Chem* (1982) 257:11256-11260, and the effect of heparin on vascular smooth muscle cell growth in fetal tissue was described by Benitz, W.E., et al., *J Cell Physiol* (1986) 127:1-7. The effect of heparin as an inhibitor of both pericyte and smooth muscle cell proliferation was shown by Orlidge, A., et al., *Microvascular Research* (1986) 31:41-53, and these authors further showed that chondroitin sulfate, and dermatan sulfate do not have this effect. A review of the effects of heparin and heparan sulfate on the proliferation of smooth muscle cells has been published by Benitz, W.E. in "The Pulmonary Circulation: Normal and Abnormal", Fishman, A.P., ed., University of Pennsylvania Press (1988).

It is not clear by what mechanism these glycosaminoglycans operate, or to what extent they interact with other growth factors such as epithelial and fibroblast growth factors. It has been proposed that a 3-O sulfate on glucosaccharide in an oligosaccharide of at least 5 sugars is important in this process and that both O-and N-sulfation is important (Castellot, J.J., et al., *J Cell Physiol* (1984) 120:315-320; Castellot, J.J., et al., *J Cell Biol* (1986) 102:1979-1984). Hexasaccharides-decasaccharides obtained from partial nitrous acid digestion of heparin bind to acidic fibroblast growth factor and aid its mitogenic activity in fibroblasts, but inhibit the proliferation of endothelial cells under some conditions (Barzu, T., et al., *J Cell Physiol* (1989) 140:538-548). The effective hexasaccharide was stated to have the structure:

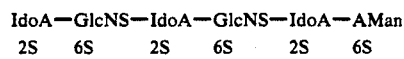

Others have indicated that the presence of 2-0-sulfate glucuronic acid is not necessary for antiproliferative activity (Wright, Jr., T.C., et al., *J Biol Chem* (1989) 264:1534-1542). In this article, size separated fragments of defined length prepared by nitrous acid cleavage and gel filtration were further separated according to charge for some assays. Partially digested heparin separated only according to size was tested with respect to stimulation of smooth muscle cells and epithelial cells. Similar results were found in both cases, although the results were not identical. Tetrasaccharides of the type tested were shown to have very low antiproliferative activity; hexasaccharides, octasaccharides and decasaccharides were shown to be active to approximately the same level on a weight/volume concentration basis. Also tested was a synthetic pentasaccharide which represents a unique sequence of the heparin-binding site in heparin to antithrombin III; this pentasaccharide was active in inhibiting proliferation for smooth muscle cells, but not for epithelial cells.

The size separated fractions were then treated chemically to produce "O-oversulfation" and this treatment enhanced the inhibitory activity; indeed, O-oversulfation of the tetrasaccharide fragment preparation caused the tetrasaccharide fraction to become active in inhibiting proliferation. The converse process, comprising desulfation and reacetylation of the amino groups or glucosamine results in a reduction in antiproliferative activity. These fragments could, however, be made more active by subsequent O-oversulfation.

Also capable of reducing the antiproliferative activity of the heparin fragments was reduction of the carboxyl groups so as to reduce the total negative charge. O-oversulfation partially, at least, restores this activity. These results with N-desulfated, N-acetylated fragments which are lacking in antiproliferative activity are distinguishable from previous results wherein similarly treated heparin retains the capacity to prevent cell division because of the size dependency of the antiproliferative activity-larger fragments being more powerful in general than smaller ones.

Finally, when the size separated fraction was then further fractionated according to charge, it was found that the most highly charged fractions showed the greatest activity. Furthermore, it was shown that although the synthetic pentasaccharide identified with the antithrombin III binding site is capable of inhibiting proliferation in smooth muscle cells, treatment of heparin which would destroy the sequence corresponding to this pentasaccharide (i.e., periodate treatment) does not destroy antiproliferative activity. As stated above, this synthetic pentasaccharide has the structure:

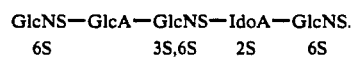

U.S. Pat. No. 4,990,502 describes the treatment of heparin with periodate, followed by depolymerization with base, and reduction of the aldehydes generated in the periodate treatment. The resulting material is said to contain a mixture of polymers containing 17-33 residues and containing a multiplicity of residues of the formula

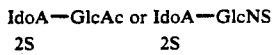

wherein the glucosamine residue is sulfated at the 2 and/or 6 position in an arbitrary manner, and wherein some of the IdoA residues may be replaced by cleaved IdoA

2S or GlcA residues resulting from the periodate oxidation. These shortened polymeric chains are said to lack the binding site for ATIII but to be capable of inhibiting smooth muscle proliferation and to have physiological activities that include acceleration of tissue repair, prevention of atherogenous lesions, prevention of states of shock, and prevention of the development of metastasis.

Treatment of heparin/heparan sulfate with periodate has also been reported by others. Fransson, L.-A. and Lewis, W., *FEBS Lett* (1979) 97:119–123, describe a variety of conditions relating to the treatment of heparin/heparan sulfate with periodate and reduction by sodium borohydride or fragmentation in alkaline medium. Fransson concluded (erroneously as will be shown hereinbelow) that the glucuronic acid residues were preferentially oxidized as compared to idouronic acid residues, and that complete cleavage of all susceptible uronic acid residues, which is said to result in pronounced fragmentation of the molecule, resulted in the absence of anticoagulant activity. Fransson, L.-A. et al., *Carbohydrate Res* (1980) 80:131–145, studied chemistry of various forms of treatment of heparin with periodate. In one study, the treatment with periodate is followed by β-elimination in base to produce fragmentation. They further report treatment of heparin with periodate followed by partial acid hydrolysis which results in fragmentation of the chains and partial destruction of the functional groups.

Casu, B. et al., *Arzneim Forsch/Drug Res* (1986) 36:637–642, studied the effect of periodate oxidation on the anti-lipemic (lipoprotein lipase-releasing) activity of heparin. In this study, the heparin was oxidized with periodate and the products were reduced with borohydride without depolymerization. The resultant was said to have the same molecular weight as the starting material. Although the ATIII binding activity of the treated material was greatly diminished, the anti-lipemic activity was said to be maintained. The amount of reduction in anticoagulant activity was said to be less for heparin derived from beef lung than that derived from porcine mucosa.

In addition to activities in releasing lipoprotein lipase and in inhibiting smooth muscle cell proliferation, heparin has been shown to inhibit platelet aggregation. This has been evidenced by the ability of heparin to prolong the bleeding time in animals. Indeed, the interference with platelet aggregation is thought to lead to an undesirable side effect of anticoagulant treatment with heparin, namely a bleeding liability with respect to some patients.

It will be noted that heparin is a complex molecule with a complex array of activities in vivo. While a particular subunit, specifically a pentasaccharide, has tentatively been designated as responsible for anticoagulant activity, heparin is also known to bind to a variety of growth factors to mediate or inhibit growth of various cell types, and may provide additional functions as yet to be ascertained. The overall structure of the molecule may be important in some degree in some or all of these. Also, the polymers generally are expected to have multiple binding sites which results in a bonding affinity not generated by a smaller fragment. Thus there is advantage in maintaining the integrity of the heparin molecule to the extent possible when destroying undesirable functions, i.e., anticoagulation properties.

The present invention provides inactivation of the anticoagulant ability of heparin without destruction of antiproliferative activity without fragmentation of the heparin chains, thus preserving to the extent possible desirable additional functions. This process has the additional advantage of retaining the size distribution of the naturally-occurring heparin/heparan sulfate preparation, which results in a therapeutic having a more readily recognized physiological profile.

DISCLOSURE OF THE INVENTION

The invention provides processes for obtaining non-anticoagulant (NAC) heparin preparations which exhibit useful antiproliferative activity and which retain the size characteristics of naturally-occurring heparin. The invention process comprises treating the heparin/heparan sulfate with periodate under conditions to effect conversion of diols on adjacent carbons to aldehydes followed by reduction of the aldehyde moieties under conditions wherein fragmentation is prevented.

The oxidation is conducted for a sufficient time that at least two-thirds of the anticoagulant activity as ascribed to binding of the heparin to antithrombin III (ATIII) is eliminated. This can be accomplished by cleavage of those glucuronic acid residues that reside in the sequence responsible for ATIII binding activity. As described hereinbelow, these glucuronic acid residues are oxidized more rapidly than glucuronic acid residues bound to the 1-position of a sulfated glucosamine.

Thus, in one aspect, the invention is directed to a process to prepare a NAC-heparin derivative, which method comprises treating heparin with periodate under conditions which effect sufficient conversion of diols on adjacent carbons to aldehydes, followed by reduction of the aldehyde moieties under conditions wherein fragmentation of the heparin oligomers does not occur so that at most ⅓ of the ATIII-binding activity of the starting material remains in resulting heparin product. Thus the product is substantially a noncoagulant (NAC) product.

In other aspects, the invention is directed to the NAC-heparin which results from the foregoing process, and to pharmaceutical compositions having the NAC heparin as active ingredient. Such compositions may be administered to a patient in order to regulate smooth muscle cell proliferation. The compositions are most advantageously formulated to be suitable for intravenous administration, adventitial administration, intravascular administration, or as implants. In still other aspects, the invention is directed to methods to treat conditions benefited by preventing smooth muscle cell proliferation using the NAC-heparin of the invention.

BRIEF DESCRIPTION OF THE DRAWINGS

FIGS. 1A and 1B show the time course of periodate oxidation of heparin under two conditions: pH 3, 4° C. and pH 6.5, 37° C.

FIGS. 2A-2D show the effect of periodate oxidation on various moieties in heparin at pH 3, 0° C.

MODES OF CARRYING OUT THE INVENTION

The invention relates to mixtures of glycosaminoglycan chains which have been oxidized with periodate and then reduced, but not fragmented, which are prepared from commercially available heparin. Described herein are methods to prepare these compositions and the nature of the resulting composition.

By "heparin/heparan sulfate" or "heparin" is meant a preparation obtained from tissues in a manner conventional for the preparation of heparin as an anticoagulant or otherwise synthesized and corresponding to that obtained from tissue. See Conrad, H.E., *Heparin and Related Polysaccharides*, Vol. 56, p. 18 of Annals of N.Y., Academy of Sc., Jun. 7, 1989, incorporated herein by reference. This preparation may include residues of D-glucuronic acid (GlcA), as characteristic of heparan sulfate as well as iduronic acid (IdoA) as characteristic of heparin. However, both GlcA and IdoA are present in both, they are present in different proportional amounts. The (IdoA)/GlcA ratio rises as heparan sulfate becomes more heparin-like. As described in the Background section above, the conversion of D-glucuronic acid to L-iduronic acid is a result of epimerization at the 5 carbon of GlcA residues in a heparan-type intermediate. This sequence of steps involved in such epimerization and conversion is understood in the art. To the extent that full conversion has not been made, heparan sulfate characteristics remain in the preparation. Because the precise nature of the polymeric chains in the preparations of heparin is not generally determined, and varies from preparation to preparation, the term "heparin/heparan sulfate" or "heparin" is intended to cover the range of mixtures encountered. Perhaps the main feature which distinguishes heparan sulfate from heparin is that the latter has anti-coagulant activity.

The "heparin/heparan sulfate" or "heparin" preparation can be obtained from a variety of mammalian tissues, including, if desired, human tissue. Generally, porcine or bovine sources are used, and vascularized tissues are preferred. A preferred source of heparin starting material is porcine intestinal mucosa, and preparations labeled "heparin" prepared from this tissue source are commercially available. In general, the heparin starting material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin starting material are found, for example, in Charles, A.F., et al., *Biochem J* (1936) 30:1927–1933, and modifications of this basic procedure are also known, such as those disclosed by Coyne, E., in *Chemistry and Biology of Heparin*, Elsevier Publishers, North Holland, New York, Lunblad, R.L., et al., eds. (1981).

"NAC-antiproliferative heparin" refers to a mixture of non-fragmented glycosaminoglycan chains obtained by treating commercially available heparin with periodate as described herein, which mixture substantially lacks anticoagulant activity but inhibits the proliferation of smooth muscle cells.

The invention composition is an unfragmented heparin/heparan sulfate derivative which is oxidized by periodate and reduced without fragmentation of the polymers. Thus, the composition contains derivatized glycosaminoglycan chains of the range of molecular weights typical for commercial heparin preparations— i.e., 5-25 kd. It is estimated that the majority of the composition comprises glycosaminoglycan chains of 10-20 kd. This corresponds to approximately 50-100 saccharide units.

In general, the heparin starting material is treated with periodate under conditions wherein the diols on adjacent carbons contained in the glycosaminoglycan structure are oxidized to the corresponding aldehydes. Any glucuronic acid or idouronic acid which does not contain either or both a 2-sulfate or 3-sulfate would therefore be "susceptible" to oxidation and cleavage. However, as shown hereinbelow, the susceptible idouronic acid residues are cleaved much more rapidly than the susceptible glucuronic acid residues. Furthermore, susceptible glucuronic acid residues which are conjugated to the reducing terminus of a GlcNS residue are much less rapidly cleaved and oxidized than those susceptible glucuronic acid residues which are linked to the reducing terminus of a GlcNAc residue. Thus, the glucuronic acid residues which reside in the typical ATIII binding saccharide sequence are preferentially oxidized, and by suitable adjustment of the time course of oxidation, a large proportion of the ATIII binding activity can be destroyed without affecting in a substantial way, the antiproliferative activity. Any free amino groups on glucosamine residues will also be oxidized; however, the majority of glucosamine residues in heparin are either sulfated or acetylated. These residues, therefore, are not affected by the periodate oxidation.

The periodate oxidation is followed by reduction of the resulting aldehydes to alcohols under conditions wherein fragmentation of the glycosaminoglycan polymer does not take place. The resultant nonanticoagulant (NAC) heparin derivative retains antiproliferative activity vis-à-vis smooth muscle cells.

In general, the periodate oxidation is performed in 0.01-0.10 M sodium periodate buffered to a pH of 3-6, preferably with 0.05-0.2 M sodium acetate or sodium phosphate buffer. Reaction mixtures containing commercially-available heparin/heparan sulfate at 0.5-10% (wt./volume) are incubated with the periodate oxidation solution at 0°-37° C. in dark amber containers for time intervals generally greater than 3 hrs. While this temperature range is workable, lower temperatures are greatly preferred, especially in the range of 0°-5° C., especially 0°-1° C. Shorter reaction times are needed for temperatures and pH values in the higher range, longer reaction times may be used for lower pH and temperatures In order to properly control the oxidation to provide the required diminution of anticoagulant activity while retaining antiproliferative properties, low pH and low temperatures are preferred so that the course of the reaction may be more accurately controlled. Excess periodate is then destroyed by addition of 100-500 mM ethylene glycol, and the reaction mixture is dialyzed against water.

Reduction is immediately effected with approximately 0.2 M of a suitable aldehyde-reducing agent, such as sodium borohydride at pH 8.5-9.5. Sodium bicarbonate buffer at approximately 0.2 M can appropriately be used to maintain this pH. It is important that the pH not be higher so that β-elimination is prevented. The concentration of the oxidized heparin in the reduction mixture is 1-20% (w/v). Excess borohydride is then destroyed by addition of concentrated HCl to approximately pH 4. The pH is then readjusted to neutrality with 2 M sodium carbonate and the product is desalted and dried.

The resulting composition contains modified but unfragmented heparin/heparan sulfate of molecular weight in the range of 5-25 kd with an average chain length of 50-100 saccharide units. The composition is a mixture of oxidation products corresponding to the original mixture of glycosaminoglycans in the heparin preparation, but is free of other biological contaminants. The composition is useful therapeutically under circumstances where antiproliferative activity is desirable. In a typical preparation, the anticoagulant activity of the original heparin/heparan sulfate preparation is reduced to less than 40 u/mg, preferably less than 5 U/mg, as opposed to 170 U/mg in the original preparation. The inhibition of smooth muscle cells by the preparation is the same as or greater than that of the original heparin on a weight basis.

LABELED FORMS OF THE INVENTION CLYCOSAMINOGLYCAN MIXTURES

The glycosaminoglycan mixtures of the invention can be provided with fluorescent, radioisotope, or enzyme labels as desired. Conventional techniques for coupling of label to carbohydrates or related moieties can be used. Such techniques are well established in the art. The labeled mixtures of the invention are useful in competitive immunoassays, as well as providing a means to trace the pharmacokinetics of the mixtures in vivo. Suitable radioisotope labels for this purpose include hydrogen$^3$, iodine$^{131}$, indium$^{111}$, technetium$^{99}$, and phosphorus$^{32}$. Suitable enzymic labels include alkaline phosphatase, glucose-6-phosphate-dehydrogenase, and horseradish peroxidase. Particularly preferred fluorescent labels include fluorescein and dansyl. A wide variety of labels of all three types is known in the art.

PREPARATION OF ANTIBODIES

Antibodies may also be prepared to the glycosaminoglycan compositions of the invention. Typically, the components of the mixture are conjugated to suitable immunogenic carriers such as BSA, KLH, rotaviral protein VP6, and the like. Techniques for conjugation of carbohydrates to protein carriers are well known in the art and include for example, reductive amination and the use of bifunctional linkers such as those marketed by Pierce Chemical Company, Rockford, Ill. The glycosaminoglycan components coupled to carriers are then administered to suitable mammalian host subjects using standard immunization protocols generally in the presence of adjuvants. Serum titers of the injected animals are periodically measured. Animals with high titers can be used as a source for antisera constituting polyclonal preparations immunoreactive with the glycosaminoglycan compositions of the invention.

If desired, monoclonal preparations may also be obtained by utilizing the antibody-secreting cells of the immunized animals, including peripheral blood lymphocytes, but preferably spleen cells, and immortalizing these cells prior to screening the supernatants for immunoreactivity to the glycosaminoglycan composition. The cells may be immortalized using standard Kohler-Millstein technology or by alternative methods such as infection with virus. The cell supernatants of the immortalized cell cultures are then screened using standard immunoassay technology for immunoreactivity with the glycosaminoglycan composition.

ADMINISTRATION AND USE

The oligosaccharide compositions of the invention are useful in therapeutic applications for treatment of conditions or diseases which are characterized by excessive and destructive smooth muscle cell proliferation. These conditions frequently occur where the subject has been exposed to trauma, such as in the case of surgical patients. The trauma caused by wounds or surgery results in vascular damage and secondary smooth muscle cell proliferation, which secondary proliferation results in vascular restenosis. This undesirable result can occur after vascular graft surgery, heart transplantation, balloon or laser angioplasty, arterial traumatic injury, postsurgical repair of muscular arteries, long-term in-dwelling of arterial catheters, invasive arterial diagnostic procedures, kidney, lung or liver transplants, coronary artery bypass surgery, carotid artery bypass surgery, femoral popliteal bypass surgery, and intracranial arterial bypass surgery.

In addition to secondary smooth muscle cell proliferation events occurring as a result of trauma, certain diseases are associated with unwanted vascular proliferation, although in these cases, too, it is assumed that some internal unknown injury has caused the secondary result. These disease states include Goodpasture syndrome, acute glomerulonephritis, neonatal pulmonary hypertension, asthma, congestive heart failure, adult pulmonary hypertension, and renal vascular hypertension.

For all these diseases and conditions, administration of suitable amounts of the compositions of the invention is useful in treatment. Administration is by typical routes appropriate for glycosaminoglycan compositions, and generally includes systemic administration, such as by injection. Particularly preferred is intravenous injection, as continuous injection over long time periods can be easily continued. Also preferred are introduction into the vascular system through intraluminal administration or by adventitial administration using osmotic pumps or implants. Typical implants contain biodegradable materials such as collagen, polylactate, polylactate/polyglycoside mixtures, and the like. These may be formulated as patches or beads. Typical dosage ranges are in the range of 0.1-10 mg/kg/hr on a constant basis over a period of 5-30, preferably 7-14, days. Particularly preferred dosage is about 0.3 mg/kg/hr, or, for a 70 kg adult, 21 mg/hr or about 500 mg/day.

Other modes of administration are less preferred but may be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium of formulations is found in *Remington's Phar-* maceutical Sciences, Mack Publishing Company, Easton, Pa., latest edition.

The compositions of the invention may also be labeled using typical methods such as radiolabeling, fluorescent labeling, chromophores or enzymes, and used in a competitive assay for the amount of antiproliferative component in a biological sample. Suitable protocols for competitive assays of analytes in biological samples are well known in the art, and generally involve treatment of the sample, in admixture with the labeled competitor, with a specific binding partner which is reactive with the analyte such as, typically, an immunoglobulin or fragment thereof. The antibodies prepared according to the invention are useful for this purpose. The binding of analyte and competitor to the antibody can be measured by removing the bound complex and assaying either the complex or the supernatant for the label. The separation can be made more facile by preliminary conjugation of the specific binding partner to a solid support. Such techniques are well known in the art, and the protocols available for such competitive assays are too numerous and too well known to be set forth in detail here.

The antibodies of the invention are useful in immunoassays, not only of the type described above involving competition between labeled composition and the analyte antiproliferation factor in the sample, but also for direct immunoassay for the factor. Alternate protocols involving direct assays are also of wide variety and well known. Typically, the analyte bound to antibody is detected by means of an additional reactive partner which bears a label or other means of detection. Thus, in typical sandwich assays, for example, the binding of the antibodies of the invention to analyte can be detected by further reaction with a labeled preparation of these same antibodies or by labeled antibody immunoreactive with this preparation by virtue of species differences.

The antibodies of the invention can also be formulated into pharmaceutical compositions and used to stimulate the growth of smooth muscle cells in subjects for which this result is desirable.

ASSAYS FOR SMOOTH MUSCLE CELL PROLIFERATIVE INHIBITION

The glycosaminoglycan compositions are verified to inhibit smooth muscle cell proliferation using any standard assay for this activity. A convenient assay, in detail, is as follows:

Solutions to be tested are made up in "complete medium", which is DMEM medium containing 10% fetal calf serum and penicillin/streptomycin.

Bovine smooth muscle cells (SMC) are isolated from bovine aorta by the method of Ross, R., J Cell Biol 350-700 cells PER well in 96-well microtiter plates in the medium above and allowed to attach for 2-4 hr. The complete medium is then replaced with DMEM supplemented with 0.1 % fetal calf serum, and the cells are incubated for an additional period of about 24 to 72 hr to arrest cell growth. The low-serum medium is then replaced with complete medium containing the test samples.

The cells are allowed to grow for up to 7 days with replicate plates sampled at regular intervals. Cell number is determined by removing the medium and washing the cells with phosphate-buffered saline, adding 75-150 ul lysis buffer, and assaying for lactate dehydrogenase (LDH) activity, as described by Brandley, B., et al., J Biol Chem (1987) 262:6431. The activity of LDH is proportional to cell number.

Verification of the lack of anticoagulant activity is also conducted using standard assays. One such convenient assay shows a failure to bind to antithrombin III. Other assays directly measure the lack of ability to inhibit blood clotting.

Antiproliferative activity is also shown in in vivo assays as follows: In assays using inhibition of smooth muscle cell proliferation in the rat carotid denuded endothelium as an index, the glycosaminoglycan preparation can be delivered IV or using EVAC disks. In either case, rats, such as Sprague-Dawley albino rats weighing about 350 gm are anesthetized and the left common carotid artery is denuded of endothelium using a 2-F balloon embolectomy catheter.

For IV delivery, a catheter is immediately connected to a 2 ml 12/day osmotic pump (ALZA Corp.) which is inserted into the left jugular vein. For EVAC delivery, an EVAC disk containing the glycosaminoglycan is placed at the adventitial surface of the injured carotid artery. Control disks are used in some animals.

Fourteen days after surgery, the animals are again anesthetized and fixed by perfusion with 2.5% glutaraldehyde. Both ballooned and nonballooned arteries are excised and fixed in 10% formalin and examined by H & E staining. The common carotid arteries are evaluated by planimetric measurements (SigmaScan) for gross determination of smooth muscle cell proliferation into the tunica intima.

EXAMPLES

The following examples are intended to illustrate but not to limit the invention.

EXAMPLE 1

Preparation of Nonanticoagulant (NAC)

Antiproliferative Heparin Mixtures

A. 20 g of porcine mucosa heparin (Ming Han heparin, 900201, 170 u/mg) was dissolved in 450 ml of distilled water and 50 ml of 1 M sodium acetate buffer, pH 5.2, was added. The solution was transferred to a 1 l amber bottle and chilled to 0° C. in an ice bath. After the temperature had equilibrated 500 ml of prechilled 0.2 M sodium periodate was added with moderate stirring.

After 15 hr at 0° C., the mixture was warmed to room temperature and 16 ml of ethylene glycol was added. The mixture was incubated for 1 hr at room temperature to destroy excess periodate.

The solution of oxidized heparin was filtered through Whatman #1 paper to remove a small amount of floculant precipitate and the filtrate was dialyzed against four changes of distilled water (vol ratio 1:10) using a 3.5 kDa cutoff membrane. The volume was then reduced to 400 ml by ultrafiltration using a Pharmacia Tangential Flow Apparatus fitted with a Nova 1 kDa molecular weight cut-off membrane.

The concentrated solution was chilled to 0° C. in an ice-water bath and 8.3 g of $NaHCO_3$ was added. A solution containing 3.78 g $NaBH_4$ in 100 ml of 0.05 M $Na_2CO_3$ pre-chilled to 0° C. was added to the reaction mixture and the reduction was allowed to proceed at 0° C. with moderate stirring. The pH of the reaction mixture was 8.5 at the beginning of the reaction and rose to 9.5 as the reaction proceeded. After 2 hr the pH was adjusted to 4.0 by addition of 6 N HCl and the mixture was allowed to stand for 30 min at room temperature to destroy the excess NaBH$_4$. Finally, the pH was adjusted to 7.0.

The solution containing the final product was dialyzed as described above and then lyophilized to dryness. The overall yield was 90% of the starting weight of heparin.

For further purification the product was dissolved in distilled water to give a 5% solution (wt/vol) and reprecipitated with 3 volumes of 99% ethanol. The precipitate was washed three times with 99% ethanol and the remaining ethanol was removed by placing the powder in the lyophilizer for 1 hr.

B. In a procedure using more dilute solutions, porcine heparin (Ming Han Batch HM900201) was periodate oxidized at a concentration of 0.8% of heparin in a reagent solution of 20 mM NaIO$_4$, 20 mM NaH$_2$PO$_4$, 20 mM Na$_2$HPO$_4$, and 0.2 M NaCl (pH 6.5). The reaction mixture was prepared by addition of 1500 ml of 1.6% heparin (25 grams) in deionized water to 1500 ml of 40 mM NaIO$_4$, 40 mM NaH$_2$PO$_4$-40 mM Na$_2$HPO$_4$, 0.4 M NaCl with moderate stirring at room temperature. The mixture was transferred to three 1 liter brown bottles immediately after the mixing. The reaction was run at 37° C. for 24 hrs in an incubator. After the reaction, excess periodate was consumed by adding 16 ml of ethylene glycol (to give a final concentration of 100 mM) to the reaction mixture and incubating at 37° C. for 1 hr.

The reaction mixture was then concentrated to 475 ml by ultrafiltration using a Pharmacia Tangential Flow Apparatus with a 1000 Dacut-off membrane. The pH of concentrated mixture was adjusted to 8.5 with 2 M Na$_2$CO$_3$ and the oxidized heparin was then reduced by addition of 17 grams of NaBH$_4$ powder to the solution (to give a final concentration of 0.5 M NaBH4). The reduction was run at 40° C. for 1 hr. After the reduction, the reaction was stopped by adjusting the pH to 3 with concentrated HCl, and the mixture was allowed to stand for 30 min at room temperature. The pH of the final solution was then adjusted to 7 by addition of 50% of NaOH.

To the final solution (600 ml), 3 volumes of absolute ethanol were added with moderate stirring. The precipitant was collected by centrifugation at 4000 g for 20 min. The pellets were washed with absolute ethanol three times. The pellets were then lyophilized to dryness (the yield was 20 grams).

The pellets were dissolved in deionized water and dialyzed against water for 48 hrs in a 1000 Da cutoff dialysis tube with three changes of water. The dialyzed material was lyophilized to dryness to generate the nonanticoagulant heparin (7 grams) as the retentate. The solutions outside of the dialysis tube were combined, concentrated, dialyzed and lyophilized to generate lyophilized dialysate (4 grams).

C. Preparation of nonanticoagulant heparin in absence of 0.2 M NaCl was carried out exactly as above, except that 0.2 M NaCl was absent during the periodate oxidation. This reaction gave 10 grams of retentate and 3 grams of dialyzate.

EXAMPLE 2

Properties of the NAC-antiproliferative Compositions

The NAC-antiproliferative heparin prepared according to paragraph A of Example 1 shows less than 5 u/mg anticoagulant activity compared to 170 u/mg for the starting material.

The NAC-antiproliferative heparin preparation in paragraphs B and C were tested using intravenous delivery in the assay described hereinabove using 29 male Sprague Dawley FBR albino rats weighing approximately 350 grams. The animals in groups 1 and 2 received the NAC-antiproliferative heparin prepared as in paragraphs B and C, respectively, at the rate of 0.3 mg/kg/hr for 14 days in lactated Ringer's solution. Group 3 received lactated Ringer's solution alone. When percent occlusion was measured, it was found that for the 10 animals in the control group (3) the lumen of the carotid artery was occluded to the extent of 21% of its cross-sectional area (21% occlusion); for the nine animals in the group receiving the NAC-antiproliferative heparin prepared as set forth in paragraph C, 2.5% occlusion occurred; for the 10 rats in the group receiving the NAC-antiproliferative heparin prepared as in paragraph B of Example 1, 5.6% occlusion occurred.

Thus, the NAC-antiproliferative heparin was as effective in preventing myointimal hyperplasia as heparin. It was also observed that no visible bleeding occurred post surgery in any of the rats, and the animals took less time to recover and looked healthier than those previously treated with whole heparin.

Additional studies on the NAC-antiproliferative preparation as set forth in paragraphs B and C of paragraphs 1 showed almost exclusively the presence of long oligomers with only a few shorter chains. Earlier preparations which resulted in significant depolymerization gave less satisfactory results.

The NAC-antiproliferative heparin prepared in paragraph B was also tested in vivo as described above when administered in the form of EVAC disks. The EVAC disk was composed of equal weights of the heparin preparation and ethylene vinyl acetate polymer.

Ten Sprague Dawley FBR albino rats weighing approximately 350 grams were prepared as described above; five rats received no treatment whereas the second five received an EVAC disk containing 12 mg of the NAC-antiproliferative heparin, prepared as in paragraph B, placed at the adventitial surface of the rat carotid artery that had been denuded of endothelium. Tests on the disk afterwards showed that about 11 mg had been delivered—i.e., about 82% of the NAC-antiproliferative heparin was released.

The five rats in the control group showed 43.7% occlusion; the five rats in the EVAC-treated group showed only 15.8% occlusion.

In an additional set of determinations conducted as above, a group of 10 control rats showed 41.4% occlusion; this was reduced to 6.2% occlusion in 6 rats which were treated with the NAC-antiproliferative heparin using the EVAC discs, containing heparin prepared as in paragraph A of Example 1. Similarly prepared NAC heparin administered using an osmotic pump at 0.3 mg/kg/hr reduced % occlusion from 39.2% in 10 control group rats to 12.3% in 9 test rats. Ethanol precipitation of the NAAC-heparin before administration resulted in 13.4% occlusion in a 7-rat test group.

The NAC-antiproliferative heparins prepared in Example 1 were also analyzed for disaccharide composition by complete hydrolysis in the presence of nitrous acid, as described in Guo, Y., and Conrad, H.E., *Anal Biochem* (1989) 176:96–104. Hydrolysis with nitrous acid cleaves at N-sulfated glucosamine residues (but not at N-acylated glucosamine residue) and converts the reducing terminus to 2,5-anhydromannose. Subsequent reduction of this residue to 2,5-anhydromannitol is used to stabilize the cleavage products in this assay. The various hydrolysis products are quantitated relative to

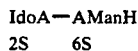

which S is known not to be destroyed in periodate oxidation and is set at 100.

A comparison of the composition of the NAC-antiproliferative composition with that of heparin is shown in Table 1. "ND" represents not detectable. As shown in Table 1, disaccharide segments susceptible to periodate oxidation (i.e., those containing unsulfated IdoA or GlcA) are completely destroyed. Those units expected not to be susceptible to periodate oxidation (those containing 2S IdoA or 2S GlcA) are retained at approximately the same ratio to the resistant standard as their occurrence in heparin.

TABLE 1

| Disaccharide | Heparin | NAC-antiproliferative |
|---|---|---|
| IdoA—AManH or GlcA—AManH | 10.0 | ND |
| IdoA—AManH 2S | 18.0 | 22.8 |
| GlcA—AManH 6S | 18.0 | ND |
| GlcA—AManH 2S | 2.6 | 2.6 |
| IdoA—AManH 6S | 12.9 | ND |
| GlcA—AManH 3S,6S | 7.4 | ND |
| IdoA—AManH 2S 6S | 100 | 100 |

EXAMPLE 3

Controlled Periodate Oxidation of Heparin

Hog mucosa heparin (anticoagulant activity= USP units/mg) was oxidized with NaIO$_4$ at 4° C. in 50 mM Na citrate buffer (pH 3.0) or at 37° C. in 50 mM Na phosphate (pH 6.5), essentially as described by Fransson et al. *Carbohyd Res* (1978) 62:235–244; and Fransson et al., *FEBS Lett* (1979) 97:119–123. Aliquots were removed from the reaction mixtures at intervals and treated with ethylene glycol to destroy unreacted NaIO$_4$. The samples were dialyzed vs water, dried by lyophilization, and reduced with NaBH$_4$.

The disaccharide and tetrasaccharide compositions obtainable by degradation of the original heparin and of the oxidized samples were measured to follow the destruction of the uronic acid residues of the heparin during the oxidization. Each sample was treated with nitrous acid at pH 1.5 and the resulting di- and trisaccharides were quantified using the reversed phase ion pairing HPLC method described previously (Guo, Y. and Conrad, H.E. *Analyt Biochem* (1989) 176:96–104). Anticoagulant activity was determined by APTT and anti-Xa assays. These assays were kindly performed by Dr. Betty Yan, Lilly Research Labs, Indianapolis, Ind., USA.

The trisulfated disaccharide that is critical for the anticoagulant activity is

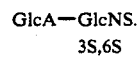

A tetrasaccharide, t14, that contains this disaccharide is

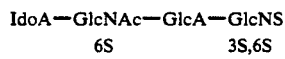

The trisulfated disaccharide, when released from the N-deacetylated heparin by treatment with nitrous acid, yields

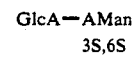

abbreviated here as GMS$_2$. Direct nitrous acid cleavage of this segment of heparin yields the tetrasaccharide, t14, and not free GMS$_2$. On the other hand, when the GMS$_2$ in heparin is situated in a position with a GlcNS residue linked to the C4 position of its GlcA, it will be released by nitrous acid without prior N-deacetylation as the free disaccharide.

Other possible degradation products and their abbreviations are:

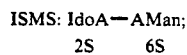

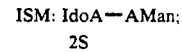

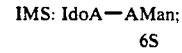

and

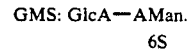

FIG. 1 shows a comparison of the rates of disappearance of the major disaccharide units of heparin at pH's 3.0 (4° C.) (FIG. 1a) and 6.5 (37° C.) (FIG. 1b). For these measurements, the samples at various time intervals were N-deacetylated and then cleaved with nitrous acid at both pH 1.5 and pH 4.0 to give total disaccharide release. Since all of the GlcN-type residues in heparin are resistant to NaIO$_4$ oxidation, the disappearance of each susceptible disaccharide is due to the oxidation of its uronic acid residue. Only those uronic acid residues that lack a SO$_4$ substituent at both C$_2$ and C$_3$ are susceptible to IO$_4^-$.

The results in FIG. 1 show (a) that the overall oxidation of susceptible uronic acids proceeds more rapidly at pH 6.5 and 37° C. than at pH 3.0 and 4° C., and (b) that under both oxidation conditions the unsulfated IdoA residues are oxidized much more rapidly than the unsulfated GlcA residues. A study of heparin oxidation at pH 5 and 4° C (not shown) gave rates similar to those observed at pH 6.5. Since the ratios of the rates of IdoA and GlcA oxidation were similar at both pH's 3.0 and 6.5, the pH 3 conditions were chosen for further examination of the oxidation of heparin, since, under the latter conditions, the progression of the reaction could be observed over a more extended time interval, allowing better control of the reaction.

The slow and incomplete oxidation of GMS$_2$ at pH 3 suggests that the anticoagulant activity of heparin should also be lost slowly and incompletely, as reported previously (Fransson, L.-A. et al. Carbohyd Res (1980) 80:131-145). To explore this further, the rates of loss of anticoagulant activity and GMS$_2$ were compared, as shown in FIG. 2.

The results shown in FIG. 2a (total disaccharides) are the same as those shown in FIG. 1a. The GMS$_2$ and t14 released by pH 1.5 nitrous acid treatment without prior N-deacetylation are shown in FIG. 2b. The GMS$_2$ disaccharide formed under the latter conditions represents "GlcNS-linked GMS$_2$"; i.e., this GMS$_2$ is formed only when there is a GlcNS residue linked to the GlcA. Oxidation associated with the acetylated form (t14) occurs much more rapidly. Subtraction of the GlcNS-linked GMS$_2$ of FIG. 2b from the total GMS$_2$ of FIG. 2a yields the GlcNAc-linked GMS$_2$, shown in FIG. 2c, all or most of which is derived from the antithrombin III-binding pentasaccharide. This is confirmed in FIG. 2d which shows loss of anticoagulant activity as measured by APTT or anti-Xa.

The results in FIGS. 2a-2d show that the GlcNAC-linked GMS$_2$ and the GlcNS-linked GMS$_2$ are oxidized at markedly different rates, and that the rate of loss of anticoagulant activity parallels the rates of disappearance of only the GlcNAc-linked GMS$_2$ and the t14 tetrasaccharide (which contains the GlcNAc-linked GMS$_2$), and not the GlcNS-linked GMS$_2$.

The analytical aspects of this work were facilitated by the recently developed methods (Bienkowski, M.J. and Conrad, H.E. J Biol Chem (1985) 260:356-365; Guo, Y. and Conrad, H.E. Analyt Biochem (1989) 176:96-104) for quantification of di- and tetrasaccharides formed when heparin is cleaved with nitrous acid before or after N-deacetylation. These approaches give a more precise measure of uronic acid residues as the oxidation proceeds than the previously used colorimetric (Fransson, L.-A. Carbohyd Res (1974) 36:339-348; Fransson, L.-A. Carbohyd Res (1978) 62:235-244; and Fransson, L.-A. and Lewis, W. FEBS Lett (1979) 97:119-123) or spectrophotometric measurements (Casu, B. et al. Arzneim-Forsch/Drug Res (1986) 36:637-642). Thus, it was possible to demonstrate that IdoA in heparin is indeed oxidized much more rapidly than most of the GlcA. This is in agreement with the results reported previously in the context of the comparison of dermatan SO$_4$ and chondroitin SO$_4$ periodate oxidation. Furthermore, the rate of IO$_4^-$ oxidation of GlcA is markedly influenced by the substitution on the amino group of the GlcN residue that is linked to C4 of the GlcA, as previously suggested (Fransson, L.-A. and Lewis, W., supra). Finally, the oxidation of the GlcNS-linked GlcA residues that yield GMS$_2$ on direct pH 1.5 nitrous acid treatment appears to be (at least) biphasic. This type of disaccharide unit therefore occurs in several different environments in heparin; one or more of these environments is not in the antithrombin III binding pentasaccharide. The final slow rate of GMS$_2$ oxidation parallels the slow loss of the residual anticoagulant activity.

EXAMPLE 6

Inhibition of VWF-Mediated Platelet Aggregation

The NAC-heparin preparation prepared as in Example 1A, but wherein periodate oxidation was conducted for 40 hrs rather than 15 hrs, was tested for its ability to inhibit the aggregation of platelets mediated by Van Willebrand factor (VWF). Platelet aggregation in response to ristocetin in the presence of purified vWF was measured in a Scienco two-channel aggregometer as described by Kelton, J.G. et al., Thromb Res (1980) 18:477-483. platelet counts were adjusted to 200,000/µL. Samples of fresh formaldehyde-fixed platelets or platelet-rich plasma were preincubated with various concentrations of test material or TBS buffer control for 10 min prior to adding ristocetin/vWF agonist. Results are expressed as percent of the maximal response of control samples and termed "aggregation" for platelet-rich plasma and "agglutination" for formaldehyde-fixed platelets.

When the preparation of NAC-heparin prepared as described above was used in this assay, the relative agglutination of platelets fell to 50% of control at a NAC-heparin concentration of less than 0.01 mg/ml. Agglutination was reduced to zero at approximately 0.025 mg/ml. In contrast, untreated heparin from Sigma (St. Louis, Mo.) was able to reduce agglutination by 50% in the same assay at 0.04 mg/ml; complete elimination of agglutination occurred only at 0.1 mg/ml. For Ming Han heparin, these values were even higher; 50% agglutination was achieved at a concentration higher than 0.1 mg/ml.

We claim:

1. A process to convert heparin or heparan sulfate having adjacent diol groups to a substantially unfragmented modified heparin or heparan sulfate having alcohol groups in place of said diol groups, said modified heparin or heparan sulfate being substantially non-anticoagulant, and an inhibitor of smooth muscle cell proliferation at concentrations equal to or lower than said heparin or heparan sulfate, said process comprising the steps of:

oxidizing glucuronic and iduronic acid of said heparin or heparan sulfate for about 15 hours at 0° C. in solution at a pH of about 5 thereby converting said diol groups to aldehyde groups under conditions that yield said modified heparin or heparan sulfate having substantially no IdoA-AManH, GlcA-AManH, GlcA-AManH 6S, IdoA-AManH 6S, or GlcA-AmanH 3S, 6S based upon disaccharide analysis of said heparin or heparan sulfate;

stopping said oxidization of said heparin or heparan sulfate;

reducing said oxidized heparin or heparan sulfate thereby converting said aldehyde groups to alcohol groups to produce said modified heparin or heparan sulfate having less than 3% of the anticoagulant activity of said heparin or heparan sulfate; and recovering said modified heparin or heparan sulfate.

2. The process of claim 1 wherein said treating with periodate is effected by incubating a solution containing 0.5-10% heparin/heparan sulfate (w/v) in 0.01-0.10 M periodate.

3. The process of claim 1 wherein said reducing is conducted by treating the oxidized heparin with sodium borohydride at about 0.1-0.3 M and pH 8-9.

4. The process of claim 1 which further includes removing excess reagents and salts prior to recovering said modified heparin or heparan sulfate.

5. The process of claim 1 wherein substantially all susceptible idouronic acid residues and substantially all glucuronic acid residues in heparan or heparin sulfate coupled to the reducing terminus of an acetyl glucosamine residue are oxidized by periodate, but wherein a plurality of glucuronic residues coupled to the reducing terminus of an N-sulfated glucosamine residue are not oxidized by periodate.

6. The process of claim 1 wherein substantially all susceptible idouronic acid and glucuronic acid residues are oxidized by periodate.

7. The process of claim 1 wherein substantially all susceptible idouronic acid residues are oxidized by periodate, but wherein a plurality of glucuronic residues are not oxidized by periodate.

8. A substantially noncoagulant, antiproliferative heparin derivative prepared by the process of claim 4.

9. A pharmaceutical composition suitable for intravenous administration which contains, as active ingredient, the noncoagulant, antiproliferative heparin of claim 8.

10. A method to treat cardiovascular conditions which are benefited by preventing smooth muscle proliferation, which method comprises administering to a subject in need of such treatment an effective amount of the heparin derivative of claim 8 or a pharmaceutical composition thereof.

11. A modified heparin or heparin sulfate produced from heparin or heparan sulfate, respectively, that has less than 3% of the anticoagulant activity of heparin or heparan sulfate and that has substantially no IdoA-AManH, GlcA-O AManH, GlcA-AManH 6S, IdoA-AManH 6S, or GlcA-AManH 3S, 6S based upon disaccharide analysis of said modified heparin or heparan sulfate, and that is an inhibitor of smooth muscle cell proliferation at concentrations equal to or lower than heparin or heparin sulfate.

12. A method to inhibit Von Willebrand Factor dependent platelet aggregation comprising contacting said platelets with an effective amount of the modified heparin or heparan sulfate of claim 11.

* * * * *